United States Patent [19]

De Both et al.

[11] Patent Number: 5,422,259

[45] Date of Patent: Jun. 6, 1995

[54] **TRANSGENIC PLANTS BELONGING TO THE SPECIES *CUCUMIS MELO***

[75] Inventors: Michiel De Both, Beaumont; Sophia Ben Tahar, Clermont-Ferrand; Marianne Noel, Clermont-Ferrand; Joël Perret, Opme Romagnat, all of France

[73] Assignee: Biosem, Ennezat, France

[21] Appl. No.: 27,563

[22] Filed: Mar. 5, 1993

Related U.S. Application Data

[63] Continuation of Ser. No. 566,255, Aug. 13, 1990, abandoned.

[30] Foreign Application Priority Data

Aug. 11, 1989 [FR] France ................ 89 10848

[51] Int. Cl.⁶ .............................. C12N 15/82
[52] U.S. Cl. ................... 435/172.3; 435/240.49
[58] Field of Search ......... 435/172.3, 240.4, 240.49; 935/52, 57

[56] References Cited

U.S. PATENT DOCUMENTS 4,672,035  6/1987  Davidonis et al. ............. 435/240.4
5,013,659  5/1991  Bedbrook et al. ............. 435/172.3

FOREIGN PATENT DOCUMENTS 0262972  10/1987  European Pat. Off. .
0265100  10/1987  European Pat. Off. .
0257993   3/1988  European Pat. Off. .
WO-8905858 6/1989  WIPO .

OTHER PUBLICATIONS

M. Cuozzo et al., *Biotechnology*, 6, 549–577 (1988).
J. Owen et al., *Virology*, 166, 495–502 (1988).
*Biological Abstracts*, BR37:95629, [G. Fang et al., *86th Annual Mtg of the Amer. Soc. for Horticultural Science*, Tulsa, Okla., Jul. 29–Aug. 3, 1989, Hort. Science, suppl. (1989)].
*Nucleic Acid Research*, (vol. 18, No. 5, Mar. 1990), Erratum, a correction of information in *Nucleic Acids Research*, 17 10492 (1989).
Biological Abstracts, vol. 79, No. 11, Abstract No. 95343 [Kreutmeier et al., Gartenbauwissenschaft, 49, 204–212 (1984)].
*Biological Abstracts*, 87, Abstract No. 12323.
K. Abak et al., *Cucurbit Genetics Cooperative Report*, 3, 27–29 (1980).
P. P. Abel et al., *Science*, 232, 738–743 (1986).
G. An et al., *EMBO J.*, 4, 277–284 (1985).
M. Bevan, *Nucleic Acids Research*, 12, 8711–8721 (1984).
L. Bouabdallah et al., *Z. Pflanzenz chtung*, 96, 82–85 (1986).
M. Branchard et al., *C.R. Acad. Sci. Paris*, 307, S rie III, 777–780 (1988).
L. Broadbent, *Ann. Rev. Phytopathol.* 14, 75–96 (1976).
R. Cade et al., *Cucurbit Genetics Cooperative Report*, 11, 3–4 (1988).
P. Chee et al., *Plant Cell Reports*, 7, 274–277 (1988).

(List continued on next page.)

*Primary Examiner*—Che S. Chereskin
*Attorney, Agent, or Firm*—Merchant, Gould, Smith, Edell, Welter & Schmidt

[57] ABSTRACT

Procedure for the production of transgenic seedlings starting from genetically transformed buds, the said seedlings belonging to the species Cucumus melo and containing at least one gene introduced through the intermediary of *Agrobacterium tumefaciens*, characterized by the culture in two successive stages of genetically transformed buds, the first of these steps taking place in a plant cell culture medium containing a cytokinin and more particularly 6-benzyl aminopurine (BAP), and the second, which is performed when the buds have attained a height of about at least 3 mm, taking place in a plant cell culture medium containing as macro-elements:

| | |
|---|---|
| $KH_2PO_4$ | about 50 to about 100 $mgL^{-1}$ |
| $MgSO_4$ | about 75 to about 300 $mgL^{-1}$ |
| $CaCl_2.2H_2O$ | about 500 to about 2500 $mgL^{-1}$ |
| $KNO_3$ | about 750 to about 1200 $mgL^{-1}$ |
| $NH_4NO_3$ | about 150 to about 200 $mgL^{-1}$ |

11 Claims, 13 Drawing Sheets

OTHER PUBLICATIONS

M. Chilton et al., *Nature*, 295, 432–434 (1982).
A. Costa et al., *Plant Dis.*, 64, 538–541 (1980).
M. Cuozzo et al., *Biotechnology*, 6, 549–557 (1988).
C. David et al., *Biotechnology*, 2, 73–76, (1984).
J. Deakin et al., *Economic Botany*, 25, 195–211 (1971).
M. T. J. De Both, *Gene Transfer by Electroporation in Plant Protoplasts and Tissues*, Abstract of Thesis, University of London (1990).
W. DeGreef et al., *Biotechnology*, 7, 61–64 (1989).
R. Dirks et al, *Plant Cell Reports*, 7, 626–627 (1989).
K. Fernow, *Phytopathology*, 57, 1347–1352 (1967).
R. Fraley et al, *Biotechnology*, 3, 629–637 (1985).
R. Fraley et al., "Genetic transformation in higher plants" *CRC Critical Rev. Plant Sciences*, 4, 1–46 (1986).
S. Hidaka et al., *J. Biochem.*, 97, 161–171 (1985).
V. Hilder et al., *Nature*, 300, 160–163, (1987).
A. Hoekema et al., *Biotechnology*, 7, 273–278 (1989).
R. Horsch et al., *Science*, 227, 1229–1231 (1985).
R. Jefferson, *EMBO Journal*, 6, 3901–3907 (1987).
S. Jelaska, *Planta (Berl.)*, 103, 278–280 (1972).
S. Jelaska, *Pysiol. Plantarum*, 31, 257–261 (1974).
R. Kathal et al., *J. Plant Physiol*, 126, 59–62 (1986).
R. Kathal et al., *Plant Cell Report*, 7, 449–451 (1988).
C. Kevers et al., *Physiol. Plant*, 61, 69–74 (1984).
Y. Kho et al., *Euphytica*, 29, 661–672 (1980).
S. Kim et al., *Plant Cell Tissue Organ Culture*, 12, 67–74 (1988).
H. Klee et al., *Ann. Rev. Plant Physio.*, 38, 467–486 (1987).
M. Lassner et al., *Plant Cell Tissue and Organ Culture* (in press) (1989).
B. Leshem et al., *Annals of Botany*, 61, 255–260 (1988).
W. A. Mackay et al., *Cucurbit Genetics Cooperative*, 11, 33–34 (1988).
S. Malepszy et al., *Pfanzenphysiologie*, 111, 273–276 (1983).
T. Maniatis et al., *Molecular Cloning—A Laboratory Manual* (1982).
G. Marchoux, *Prop rti s biologieques et genetiques des ARN du virus de la mosa que du concombre*, Th se de Docteur s Science naturelles (1975).
V. Moreno et al., *Plant Cell Tissue and Organ Culture*, 5, 139–146 (1985).
W. Msikita et al., *Curbit Genetics Cooperative Report*, 11, 5–7 (1988).
T. Murashige et al., *Physiologia Plantarum*, 15, 473–497 (1962).
R. Niedz et al., *Plant Cell Tissue and Organ Culture* (in press) (1989).
T. Oridate et al., *Japan J. Breeding*, 36 424–428 (1986).
M. Orts et al., *Hort Science*, 22, 666 (1987).
K. Rajasekaran et al., *Annals of Botany*, 52, 417–420 (1983).
S. Scharf et al., *Science*, 233, 1076–1078 (1986).
S. Smith et al., *Abstract Proc. Annual TCA Meeting*, Las Vagas, Nevada, (1988).
E. John Staba, "Plant Tissue Culture as a Technique for the Phytochemist" in *Recent Advances in Phytochemistry*, vol. 2, Ed.: Seikel and Runeckels, Appleton century-crofts, New York (1969), pp. 75–106.
S. B. Tahar et al., "Introduction of foreign genes into melon (*Cucumis melo* L.) using *Acrobacterium tumefaciens*" *Proc. Cucurbitaceae.* France (1988).
N. E. Tumer et al., *EMBO J.*, 6, 1181–1188 (1987).
M. Vaeck et al., *Nature*, 328, 33–37 (1987).
C. Van Dun et al., *Virology*, 167, 649–652 (1988).
L. W. D. Van Raamsdonk, *Prophyta*, 6, 231–232 (1989).
T. Wehner et al., *Hort Science*, 16, 759–760 (1981).
H. Ezura et al., "Efficient Production of Tetraploid Melon (*Cucumis melo* L.) by Somatic Embryogenesis", *Japan J. Breed.*; 42, 137–144 (1992).
H. Ezura et al., "Highly Frequent Appearance of Tetraploidy in Regenerated Plants, a Universal Phenomenon, in Tissue Cultures of Melon (*Cucumis melo* L.), *Plant Science*, 85, 209–213 (1992).
S. Ben Tahar et al., "Introduction of Foreign Genes Into Melon (*Cucumis melo* L.) using *Agrobacterium tumefaciens*", *Proc. Cucurbitaceae.* France (1988).
de Both et al., "Towards a System for the Regeneration and Transformation of Melon (*Cucumis melo* L.) *Congress Proceedings of the International Bucarpia; Congress on Genetic Manipulation in Plant Breeding*, 1–6, New York: Plenum Press (1989).
Kreutmeier et al. (1985) Biological Abstract 79 (11), 410, Abstract No. 95343.
Ammirato in Handbook of Plant Cell Culture, vol. 1 (Evans, et al, eds.) MacMillan, New York, 1983, pp. 99–100.
Fang et al. (1990) Plant Cell Reports 9: 160–164.

```
GTTATTGTCTACTGACTATATAGAGAGTGTTTGTGCTGTGTTTCTCTTTT                              51

GTGTCGTAGAATTGAGTCGAGTC ATG GAC AAA TCT GAA TCA ACC                             95
                        Met Asp Lys Ser Glu Ser Thr                              7

AGT GCT GGT CGT AAC CGT CGA CGT CGT CCG CGT CGT GGT                             134
Ser Ala Gly Arg Asn Arg Arg Arg Arg Pro Arg Arg Gly                              20

TCC CGC TCC GCC CCC TCC GCG GAT GCT AAC TTT AGA                                 173
Ser Arg Ser Ala Pro Ser Ser Ala Asp Ala Asn Phe Arg                              33

GTC TTG TCG CAG CAG CTT TCG CGA CTT AAT AAG ACG TTA                             212
Val Leu Ser Gln Gln Leu Ser Arg Leu Asn Lys Thr Leu                              46
```

FIG. 2A

```
GCA GCT GGT CGT CCA ACT ATT AAC CAC CCA ACC TTT GTA    251
Ala Ala Gly Arg Pro Thr Ile Asn His Pro Thr Phe Val     59

GGG AGT GAA CGC TGT AGA CCT GGG TAC ACG TTC ACA TCT    290
Gly Ser Glu Arg Cys Arg Pro Gly Tyr Thr Phe Thr Ser     72

ATT ACC CTA AAG CCA CCA AAA ATA GAC CGT GGG TCT TAT    329
Ile Thr Leu Lys Pro Pro Lys Ile Asp Arg Gly Ser Tyr     85

TAC GGT AAA AGG TTG TTA CTA CCT GAT TCA GTC ACG GAA    368
Tyr Gly Lys Arg Leu Leu Leu Pro Asp Ser Val Thr Glu     98
```

FIG. 2B

```
TAT GAT AAG AAG CTT GTT TCG CGC ATT CAA ATT CGA GTT    407
Tyr Asp Lys Lys Leu Val Ser Arg Ile Gln Ile Arg Val    111

AAT CCT TTG CCG AAA TTT GAT TCT ACC GTG TGG GTG ACA    446
Asn Pro Leu Pro Lys Phe Asp Ser Thr Val Trp Val Thr    124

GTC CGT AAA GTT CCT GCC TCC TCG GAC TTA TCC GTT GCC    485
Val Arg Lys Val Pro Ala Ser Ser Asp Leu Ser Val Ala    137

GCC ATC TCT GCT ATG TTC GCG GAC GGA GCC TCA CCG GTA    524
Ala Ile Ser Ala Met Phe Ala Asp Gly Ala Ser Pro Val    150
```

FIG. 2C

```
CTG GTT TAT CAG TAT GCC GCA TCT GGA GTC CAA GCC AAC   563
Leu Val Tyr Gln Tyr Ala Ala Ser Gly Val Gln Ala Asn   163

AAC AAA CTG TTG TAT GAT CTT TCG GCG ATG CGC GCT GAT   602
Asn Lys Leu Leu Tyr Asp Leu Ser Ala Met Arg Ala Asp   176

ATA GGT GAC ATG AGA AAG TAC GCC GTC CTC GTG TAT TCA   641
Ile Gly Asp Met Arg Lys Tyr Ala Val Leu Val Tyr Ser   189

AAA GAC GAT GCG CTC GAG ACG GAC GAG CTA GTA CTT CAT   680
Lys Asp Asp Ala Leu Glu Thr Asp Glu Leu Val Leu His   202
```

FIG. 2D

```
GTT GAC ATC GAG CAC CAA CGC ATT CCC ACA TCT GGA GTG       719
Val Asp Ile Glu His Gln Arg Ile Pro Thr Ser Gly Val       215

CTC CCA GTC TGATTCCGTGTTCCCAGAATCCTCCCTCCGATCTCTGTGG      768
Leu Pro Val                                               218

CGGGAGCTGAGTTGGCAGTTCTGCTATAAACTGTCTGAAGTCACTAAACGTT      820

TTTTACGGTGAACGGGTTGTCCATCCAGCTTACGGCTAAAATGGTCAGTCGT      872

GGAGAAATCCACGCCAGCAGATTTACAAATCTCTGAGGCGCCTTTGAAACCA      924

TCTCCTAGGTTTCTTCGGAAGGACTTCGGTCCGTGTACCTCTAGCACAACGT      976
```

FIG. 2E

```
AGAGAGTGTGTGTGCTGTGTTTCTCTTTGTCGTAGAATTGAGTCGAG                    51

TC ATG GAC AAA TCT GAA TCA ACC AGT GCT GGT CGT AAC                 89
   Met Asp Lys Ser Glu Ser Thr Ser Ala Gly Arg Asn                 12

CGT CGA CGT CGT CCG CGT GGT TCC CGC TCC GCC CCC                   128
Arg Arg Arg Arg Pro Arg Gly Ser Arg Ser Ala Pro                    25

TCC TCC GCG GAT GCT AAC TTT AGA GTC TTG TCG CAG CAG               167
Ser Ser Ala Asp Ala Asn Phe Arg Val Leu Ser Gln Gln                38

CTT TCG CGA CTT AAT AAG ACG TTA GCA GCT GGT CGT CCA               206
Leu Ser Arg Leu Asn Lys Thr Leu Ala Ala Gly Arg Pro                51
```

FIG. 3A

```
ACT ATT AAC CAC CCA ACC TTT GTA GGG AGT GAA CGC TGT    245
Thr Ile Asn His Pro Thr Phe Val Gly Ser Glu Arg Cys     64

AGA CCT GGG TAC ACG TTC ACA TCT ATT ACC CTA AAG CCA    284
Arg Pro Gly Tyr Thr Phe Thr Ser Ile Thr Leu Lys Pro     77

CCA AAA ATA GAC CGT GGG TCT TAT TAC GGT AAA AGG TTG    323
Pro Lys Ile Asp Arg Gly Ser Tyr Tyr Gly Lys Arg Leu     90

TTA CTA CCT GAT TCA GTC ACG GAA TAT GAT AAG AAG CTT    362
Leu Leu Pro Asp Ser Val Thr Glu Tyr Asp Lys Lys Leu    103

GTT TCG CGC ATT CAA ATT CGA GTT AAT CCT TTG CCG AAA    401
Val Ser Arg Ile Gln Ile Arg Val Asn Pro Leu Pro Lys    116
```

FIG. 3B

```
TTT GAT TCT ACC GTG TGG GTG ACA GTC CGT AAA GTT CCT    440
Phe Asp Ser Thr Val Trp Val Thr Val Arg Lys Val Pro    129

GCC TCC TCG GAC TTA TCC GTT GCC GCC ATC TCT GCT ATG    479
Ala Ser Ser Asp Leu Ser Val Ala Ala Ile Ser Ala Met    142

TTC GCG GAC GGA GCC TCA CCG GTA CTG GTT TAT CAG TAT    518
Phe Ala Asp Gly Ala Ser Pro Val Leu Val Tyr Gln Tyr    155

GCC GCA TCT GGA GTC CAA GCC AAC AAA CTG TTG TAT        557
Ala Ala Ser Gly Val Gln Ala Asn Lys Leu Leu Tyr        168

GAT CTT TCG GCG ATG CGC GCT GAT ATA GGT GAC ATG AGA    596
Asp Leu Ser Ala Met Arg Ala Asp Ile Gly Asp Met Arg    181
```

FIG. 3C

```
AAG TAC GCC GTC CTC GTG TAT TCA AAA GAC GAT GCG CTA    635
Lys Tyr Ala Val Leu Val Tyr Ser Lys Asp Asp Ala Leu    194

GAG ACG GAC GAG CTA GTA CTT CAT GTT GAC ATC GAG CAC    674
Glu Thr Asp Glu Leu Val Leu His Val Asp Ile Glu His    207

CAA CGC ATT CCC ACG TCT GGA GTG CTC CCA GTC TGATTCGT   715
Gln Arg Ile Pro Thr Ser Gly Val Leu Pro Val            218

GTTCCCAGAATCCTCCTCCGATCTCTGTGGGCGAGCTGAGTTGGCAGTTC     767

TGCTATAAACTGTCTGAAGTCACTAAACGTTTTTACGGTGAACGGGTTGTCC   819
```

FIG. 3D

ATCCAGCTTACGGGCTAAATGGTCAGTCGTGGAGAAATCCACGGCCAGTAGAT 871

TTACAAATCTCTGAGGCGCCTTTGAAACCATCTCCTAGTTTCTTCGGAAGG 923

ACTTCGGTCCGTGTACCTCTAGCACAACGTGCTAGTTTCAGGGTACGGGTGC 975

CCCCCCACTTTCGTGGGGCCTCCAAAAGGAG 1007

TRANSGENIC PLANTS BELONGING TO THE SPECIES *CUCUMIS MELO*

This is a continuation of application Ser. No. 07/566,255, filed Aug. 13, 1990, now abandoned.

This invention describes a process for the genetic transformation of plants belonging to the genus Cucumis, and in particular of the melon (Cucumis melo). This process involves the transformation of explants by *Agrobacterium tumefaciens* and the in vitro regeneration of the transformed plants.

This process of transformation and regeneration can be used to introduce a gene for resistance to the cucumber mosaic virus, for example, in plants belonging to the species Cucumis melo.

In many cases, the transfer of genetic characters from one plant species to another is limited by incompatibility barriers.

Such problems are encountered particularly in the genera Cucumis (the melon and the cucumber) and Cucurbita (the squash) of the family Cucurbitaceae. Thus, the transfer of agronomically beneficial characters such as resistance to vital diseases or insects, present in wild-type species, cannot be transferred to cultivated species.

Among the cultivated species of the genus Cucumis, sexual crosses are only possible between C. sativus (the cucumber) and the closely related species C. hardwickii and C. Sikkimensis (Deakin et al., 1971; Van Raamsdonk, 1989). In most cases, the crosses of *C. sativus* with other wild-type species give only sterile fruits; however, the melon (Cucumis melo) appears to be a refractory species which cannot be crossed with any other species (Kho et al., 1980; Van Raamsdonk, 1989).

The applications of the novel techniques of genetic engineering offer a promising alternative for the introduction of new characters with a view to improving plant species. These techniques include genetic transformation by the introduction of one or more foreign genes, somatic hybridization by fusion of protoplasts and the induction of somaclonal variations of mutations in order to induce genetic modifications.

The transfer of foreign genes into plant species is quite commonly done by using strains of *Agrobacterium tumefaciens* containing a disarmed Ti plasmid (Fraley et al., 1986) (Klee et al., 1987) (Horsch et al., 1985). Hitherto, a large variety of transgenic plants has been obtained with *Agrobacterium tumefaciens*. This bacterium enables a foreign gene to be transferred to plant cells which can regenerate transformed plants. Genes coding for profitable agronomic characters have been introduced into plant species. Thus, it has been possible to obtain plants resistant to herbicides (Degreef et al., 1989) and insects (Hilder et al., 1987; Vaeck et al., 1987).

The transfer of genes can be made either from a disarmed Ti plasmid, after homologous recombination, by using intermediate vectors (Fraley et al., 1985) or from a binary vector with the aid of a disarmed Ti plasmid (Bevan, 1984; Fraley et al., 1986).

This transfer of genes can also be carried out by the utilization of Agrobacterium rhizogenes which induces roots from the transformed tissue instead of transgenic plants. Plants having an abnormal phenotype can be regenerated from these transformed roots (Chilton et al., 1982, David et al., 1984).

A particularly interesting character is resistance to viral diseases. Genetically transformed plants resistant to different viruses have been obtained (Powell Abel et al., 1986) (Cuozzo et al., 1988) (Turner et al., 1987) (Hoekema et al., 1989) (Van Dun and Bol., 1988). These plants (tobacco, potato and tomato) express a gene coding for the capsid protein of the virus to which they are resistant. The mechanism of protection has still not been elucidated.

The standard method for protecting plants against viral diseases consists of inoculating plants with an attenuated strain of the virus in order to prevent infection by more virulent strains. This practice, called cross-protection, has enabled yield losses due to viral infections to be reduced (Broadbent 1976) (Fernow 1967) (Costa and Miller 1980).

A system for regeneration of plants from individual cells or explants, placed in culture, is essential for the application of the techniques of genetic engineering.

Such methods have been described recently for the regeneration of non-transformed Cucurbitaceae:

The regeneration of the cucumber (Cucumis sativus), after induction of adventitious shoot buds on calliderived from cotyledons, has been described (Msikita et al., 1988; Kim et al., 1988); Wehner and Locy (1981) had previously described the induction of buds on cotyledons. Cucumber plants could be regenerated by somatic embryogenesis. These somatic embryos developed either in cell suspensions derived from calli developed from leaf explants (Chee and Tricoli, 1988) or hypocotyls (Rajasekaran et al., 1983), or directly on cotyledonous (Cade et al., 1988) or leaf (Malepszy and Nadolska-Orczyk, 1983) calli. In all of the cases described above, the plant material is required to pass through a phase of callus formation and cellular dedifferentiation. A prolonged period spent in the phase of callus formation can induce undesirable somaclonal variations. In some cases, these variations can cause sterility in the regenerated plants.

In the case of the melon (C. melo), regeneration through organogenesis has already been described either directly on cotyledons placed in culture (Smith et al., 1988; Niedz et al., in press; Dirks and Van Buggenum, 1989), or through the intermediary of calli derived from cotyledons (Mackay et al., 1988; Moreno et al., 1985; Orts et al., 1987; Bouabdallah and Branchard, 1986), hypocotyls (Abak and Dumas de Vaulx, 1980; Kathal et al., 1986) or leaves (Kathal et al., 1988).

The-production of melon plants derived from somatic embryos has also been reported (Oridate and Oosawa, 1986; Branchard and Chateau, 1988).

All of these techniques require the passage through a relatively long step of dedifferentiation and callus formation which will precede the differentiation of buds or embryos. Such buds can develop and give rise either to plants having an abnormal phenotype or to sterile plants (Bouabdallah and Branchard, 1986). Furthermore, the induction of embryos or buds derived from calli is weaker than the direct induction of buds on cotyledons.

A regeneration procedure has also been described in another species of Cucurbitaceae: the squash (Cucurbita pepo) (Jelaska, 1972, 1974). This author has obtained plants starting from somatic embryos derived from calli cultivated for several months.

As far as the regeneration of genetically transformed plants is concerned, EP-A-0262972 describes the transformation of Cucumis sativus (cucumber) by means of Agrobacterium rhizogenes followed by regeneration and EP-A-0265100 describes the transformation of Cucumis sativus by fusion of protoplasts, followed by regeneration.

De Both and Ben Tahar (1989) have reported the production of transformed calli of melon. These calli which develop in the presence of kanamycin and express the gene for β-glucuronidase could not develop transgenic plants, in spite of the use of an experimental protocol already used with success in the regeneration of non-transformed melons.

The production of transgenic plants in the species Cucumis melo has never been reported.

The fact that, at present, there does not exist a method of regeneration starting from transformed tissues in the species Cucumis melo prevents transgenic melon plants from being obtained which express agronomically profitable characters such as resistance to viral diseases.

One of the objectives of the invention is to realize the regeneration of transgenic plants belonging to the species Cucumis melo.

Another objective of the invention is to define the culture media which are necessary at each step for the regeneration of transgenic plants belonging to the genus Cucumis.

This invention applies more particularly to the genetic transformation of cotyledons, hypocotyls, leaves of the species Cucumis melo through the use of *Agrobacterium tumefaciens* followed by the induction of buds and the production of genetically transformed plants. The genetic transformation of the different tissues described above, followed by organogenesis, enables the cultivated species and, more particularly, the species Cucumis melo to be improved. The plants regenerated under the conditions described in this invention have a normal phenotype and are fertile.

Another object of this invention is to transform the melon genetically in order to introduce a gene for resistance to the cucumber mosaic virus (CMV).

These objectives are attained by the procedure according to the invention.

The invention relates to a procedure for the production of transgenic plantlets starting from genetically transformed shoot buds, the said plantlets belonging to the species Cucumis melo and containing at least one gene introduced by the intermediary of Agrobacterium tumefaciens characterized by the culture of genetically transformed shoot buds in two successive stages, the first of these stages of culture taking place in a plant cell culture medium containing a cytokinin, and more particularly 6-benzyl aminopurine (BAP), and the second, which is performed when the shoot buds have attained a height of about at least 3 mm, taking place in a plant cell culture medium containing as macroelements:

| | |
|---|---|
| KH$_2$PO$_4$ | about 50 to about 100 mgL$^{-1}$ |
| MgSO$_4$ | about 75 to about 300 mgL$^{-1}$ |
| CaCl$_2$.2H$_2$O | about 500 to about 2500 mgL$^{-1}$ |
| KNO$_3$ | about 750 to about 1200 mgL$^{-1}$ |
| NH$_4$NO$_3$ | about 150 to about 200 mgL$^{-1}$ |

The invention also relates to a procedure for the induction of genetically transformed shoot buds starting from genetically transformed explants which contain at least one gene introduced by means of *Agrobacterium tumefaciens*, the said explants being derived from a plant of the species Cucumis melo, the induction being performed in a medium for the induction of genetically transformed shoot buds containing all of the mineral salts and vitamins normally required for the induction of buds starting from genetically non-transformed explants and including calcium chloride as one of the mineral salts and bacto-agar or agar-agar, characterized in that the CaCl$_2$ content of this medium is about 440 to about 2200 mgL$^{-1}$ calculated as CaCl$_2$.2H$_2$O and that of bacto-agar or agar-agar is about 0.8 to about 1.2%, the said induction medium being supplemented with about 0.3 to about 1.13 mgL$^{-1}$ 6-benzyl aminopurine (BAP) and 0 to about 1.3 mgL$^{-1}$ indole-3-acetic acid (IAA).

According to a preferred embodiment of the invention, this process for the induction of transformed shoot buds is performed in an induction medium, the calcium content of which varies from about 1000 to about 2200 mgL$^{-1}$, and more particularly from about 1750 to about 2200 mgL$^{-1}$.

By performing the process of the invention, an explant of a plant belonging to the species Cucumis melo can be transformed and regenerated as transgenic plants. The invention also relates to the transgenic plants, the transgenic plantlets, the transformed shoot buds and the transformed explants obtainable by the procedures of the invention, as well as the seeds.

FIGS. 2 is the nucleotide sequence coding for the capsid protein of the FNY strain of the cucumber mosaic virus;

FIG. 3 is the nucleotide sequence coding for the capsid protein of the I17F strain of the cucumber mosaic virus.

Figure 5:
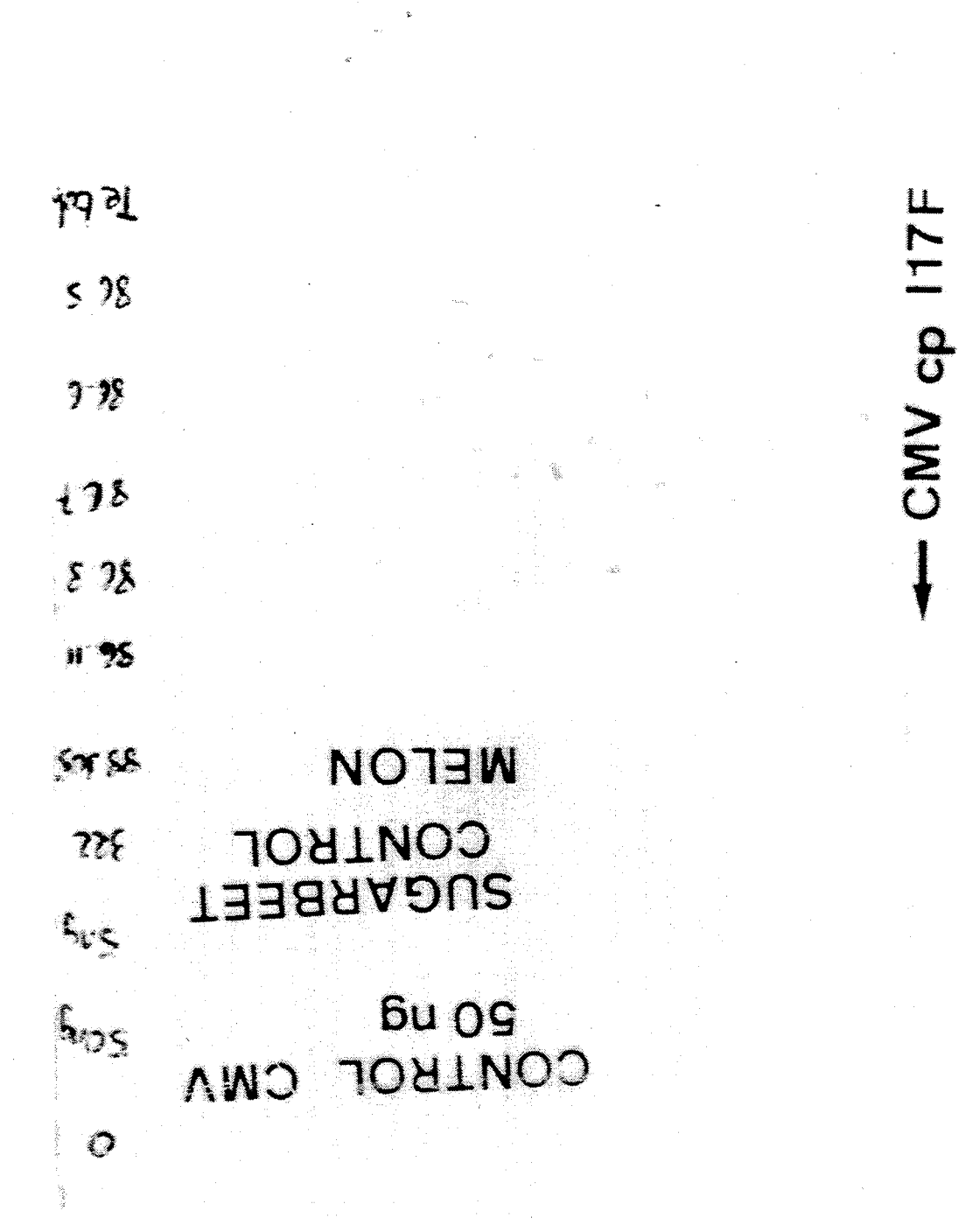

FIG. 5 is a "western blot" showing the immunoreactive bands detected with antibodies against the CMV strain I17F; and The regeneration of transformed or non-transformed plants starting from explants involves several stages of cell culture, each stage requiring a culture medium, additives, for example cytokinins, and very well-defined culture conditions and which often vary depending on the species to be regenerated and the 'pathway' of regeneration (i.e. by means of organogenesis or somatic embryogenesis, for example).

Even if a set of media and conditions is known for the regeneration of a non-transformed plant, it is impossible to know in advance whether these same media and conditions will be applicable with success to the regeneration of the plant when this latter is in the transformed state. The additional step of transformation requires the use of other media, such as transformation and co-culture media, and other additives, for example cefotaxime, which can exert an effect on the behaviour of the cells in the media and under the conditions to be used in the subsequent stages. The liability of the transformed plants to vitrification is also an element which sometimes requires the development of special conditions.

Vitrified plants are characterized by a whole range of morphological and physiological abnormalities resulting from in vitro culture conditions. The causes often cited to explain vitrification are:

too high a concentration of $NH_4^+$ ions or cytokinins
too low a concentration of agar (or other gelling substance) in the medium
a sensitivity to ethylene produced by the plant and which is found in the volume of the culture medium (Meyers et al., 1984).

The vitrification of the melon seedling cultures in vitro due to the presence of cytokinins in the medium has been reported by Leshem et al. (1984).

All of these items thus make the development of a set of media and conditions which leads to the regeneration of a transgenic plant extremely complex.

The inventors have succeeded in formulating an induction medium for shoot buds which enables genetically transformed shoot buds to be induced from transformed explants. This medium is an induction medium for shoots buds containing all of the mineral salts and vitamins normally required for the induction of buds from genetically non-transformed explants and contains calcium chloride as one of the mineral salts and bacto-agar or agar-agar, the $CaCl_2$ content of this medium varying from about 440 to about 2200 $mgL^{-1}$ calculated as $CaCl_2.2H_2O$ and that of bacto-agar or agar-agar varying from about 0.8 to about 1.2%. This induction medium is supplemented with about 0.3 to about 1.13 $mgL^{-1}$ 6-benzyl aminopurine (BAP) and about 0 to about 1.3 $mgL^{-1}$ indole-3-acetic acid (AIA).

Figure 4:
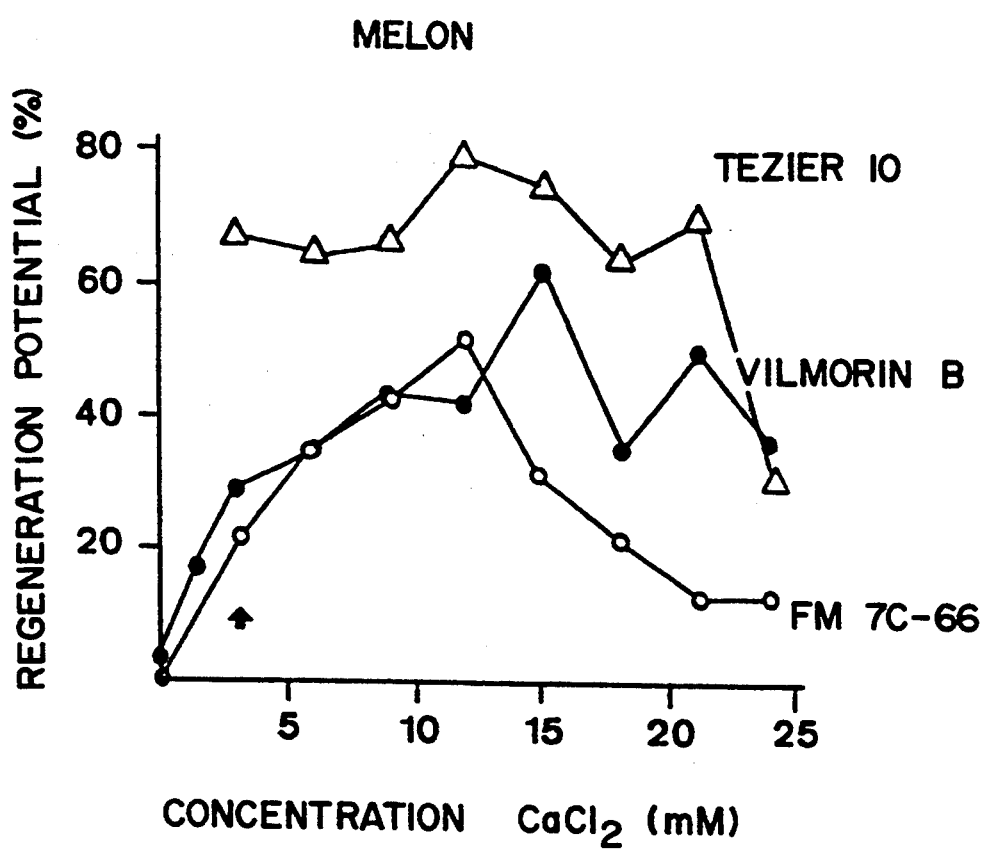
FIG. 4 is a plot of regeneration potential (%) (y-axis) vs. concentration CaCl$_2$(mM) (x-axis) depicting the influence of the concentration of CaCl$_2$ on the induction of shoot buds of melons of different genotypes.

The induction medium particularly preferred is an induction medium, the calcium content of which varies from about 1000 to about 2200 $mgL^{-1}$, and more particularly from about 1750 to about 2200 $mgL^{-1}$. The calcium concentrations represent an approximately four to five fold increase in the concentrations usually used in induction media. Generally speaking, the inventors have observed that high calcium concentrations have a very beneficial effect on the stages of regeneration of the transformed melon. FIG. 4 shows the effect of different concentrations of calcium on the induction of buds in different genotypes of the melon.

According to one embodiment of the invention, the induction medium for buds may be the medium of Murashige and Skoog (1962), known as the MS medium, the $CaCl_2$ and bacto-agar or agar-agar contents of which are modified, if necessary, within the limits specified above. The unmodified MS medium has the following composition:

| MS medium | $(mgL^{-1})$ |
| --- | --- |
| $(NH_4)NO_3$ | 1.650 |
| $KNO_3$ | 1.900 |
| $CaCl_2.2H_2O$ | 440 |
| $MgSO_4.7H_2O$ | 370 |
| $KH_2PO_4$ | 170 |
| $FeSO_4.7H_2O$ | 27.8 |
| $Na_2EDTA$ | 33.6 |
| $MnSO_4.4H_2O$ | 22.3 |
| $ZnSO_4.7H_2O$ | 8.6 |
| $H_3BO_3$ | 6.2 |
| KI | 0.83 |
| $Na_2MoO_4.2H_2O$ | 0.25 |
| $CuSO_4.5H_2O$ | 0.025 |
| $CoCl_2.6H_2O$ | 0.025 |
| myo-inositol | 100 |
| nicotinic acid | 0.5 |
| pyridoxin HCl | 0.5 |
| thiamine HCl | 0.1 |
| glycine | 2.0 |
| sucrose | 0.000 |
| pH | 5.7 |

In addition, the solidified MS medium contains 0.8% agar-agar or bacto-agar.

The preferred induction medium is the MS medium, supplemented with 0.3 to 1.13 $mgL^{-1}$ BAP, and more particularly with 0.85 mg/L BAP in the absence of any other cytokinin.

The vitamins present in the induction medium may be those normally present in the MS medium. According to another embodiment of the invention, these vitamins may be the 'Staba' vitamins (Staba, 1969).

| "Staba" vitamins | |
| --- | --- |
| nicotinamide | 2 $mgL^{-1}$ |
| pyridoxin-HCl | 2 $mgL^{-1}$ |
| d-biotin | 1 $mgL^{-1}$ |
| Ca-panthothenate | 1 $mgL^{-1}$ |
| thiamine-HCl | 1 $mgL^{-1}$ |
| choline chloride | 1 $mgL^{-1}$ |
| p-amino benzoic acid | 0.5 $mgL^{-1}$ |
| folic acid | 0.5 $mgL^{-1}$ |
| riboflavin | 0.5 $mgL^{-1}$ |
| cyanocobalamin | 1.5 $\mu gL^{-1}$ |

The induction medium for buds particularly preferred is the medium called "M.I. Medium" developed by the inventors. The M.I. medium has the following composition:

| M.I. medium | |
| --- | --- |
| Macro-elements: | |
| $KNO_3$ | 1900 $mgL^{-1}$ |
| $NH_4NO_3$ | 1650 |
| $CaCl_2.2H_2O$ | 2200 |
| $MgSO_4.7H_2O$ | 370 |
| $KH_2PO_4$ | 170 |
| $Na_2EDTA$ | idem MS |
| Micro-elements | idem MS |
| Vitamins | Staba |
| Myo-inositol | 100 $mgL^{-1}$ |
| Sucrose | 30 $gL^{-1}$ |
| Agar-agar | 0.8% |
| BAP | 3.75 $\mu M$ |
| ABA | 1 $\mu M$ |

The agar content of the solidified M.I. medium may vary from 0.8% to 1% (wt/v). 0.8% is preferred. It is possible to add about 1 $\mu M$ of abscissic acid to the induction media according to the invention.

Another medium developed by the inventors is that which enables transgenic seedlings to be obtained from transformed buds.

This medium is a plant cell culture medium which contains as mineral macro-elements:

| | |
| --- | --- |
| $KH_2PO_4$ | about 50-about 100 $mgL^{-1}$ |
| $MgSO_47H_2O$ | about 75-about 300 $mgL^{-1}$ |
| $CaCl_2.2H_2O$ | about 500-about 2500 $mgL^{-1}$ |
| $KNO_3$ | about 750-about 1200 $mgL^{-1}$ |
| $NH_4NO_3$ | about 150-about 200 $mgL^{-1}$ |

The other constituents of the medium, for example microelements, vitamins, etc. are those normally used in cell culture media, for example the MS medium, and in the usual concentrations. The sucrose content may be reduced to about 10 $gL^{-1}$.

In the preferred embodiment of the invention, the medium for the development of transgenic seedlings contains as macro-elements:

| | |
|---|---|
| KH$_2$PO$_4$ | 85 mgL$^{-1}$ |
| MgSO$_4$.7H$_2$O | 185 mgL$^{-1}$ |
| CaCl$_2$.2H$_2$O | 1720 mgL$^{-1}$ |
| KNO$_3$ | 950 mgL$^{-1}$ |
| NH$_4$NO$_3$ | 165 mgL$^{-1}$ |

It is to be noted that the CaCl$_2$.2H$_2$O content according to this aspect of the invention is about five fold higher than in standard media. On the other hand, the concentrations of KH$_2$PO$_4$, MgSO$_4$.7H$_2$O and KNO$_3$ are about half of that found in other media of this type, and that of NH$_4$NO$_3$ is about one tenth.

A particularly preferred medium of the invention for the development of the transgenic seedlings is the medium called MB6, the composition of which is given in Table 1.

This medium, developed by the inventors, is essential for obtaining transgenic plantlets from shoot buds. However, it is important that the shoot bud culture be performed in two stages, the first of these stages taking place in an initial plant cell culture medium containing a cytokinin. The cytokinin may be kinetin or BAP. BAP is particularly preferred. An appropriate initial cell culture medium is, for example, the MS medium supplemented with 0.1–1.2 mgL$^{-1}$, and in particular about 0.2 mgL$^{-1}$, BAP. This culture medium is normally solidified by the addition of about 0.8% agar-agar or bacto-agar.

When the buds have attained a height of about 3 mm or more in this initial medium, they are transferred to a second medium which is the medium defined in detail above, for example the MB6 medium, enabling transgenic plantlets to be obtained. This medium will be called 'the medium of the MB6 type' herein after.

In this medium of the MB6 type, the buds at least 3 mm high grow taller and after about 4 weeks the plantlets take root. Once the lateral roots have developed in this medium, the plants can be transferred to pots containing a mixture of compost and coarse sand and placed in culture in a greenhouse. The transgenic plants thus obtained have a normal phenotype and are fertile.

The media of the invention are, of course, supplemented, if necessary, with agents permitting the selection of transformants, for example antibiotics, and agents which inhibit the growth of *A. tumefaciens*, for example cefotaxime. The concentrations of cefotaxime which may be used are of the order of about 200 mgL$^{-1}$ to about 400 mgL$^{-1}$. The simultaneous application of a selection with kanamycin makes it possible to use about 200 mgL$^{-1}$ of cefotaxime for the inhibition. It is particularly preferred to use 200 mgL$^{-1}$ of cefotaxime since the development of the seedlings is not affected by this relatively low concentration. The concentrations of kanamycin used may vary between about 50 and 400 mgL$^{-1}$. If the M.I. medium is used as selection medium, the kanamycin concentration must lie between 150 mgL$^{-1}$ and 400 mgL$^{-1}$.

According to one embodiment of the invention, the induction medium for buds and the medium of the MB6 type can be used successively for the regeneration of transgenic melon plants from transformed explants. The buds induced by culture in the induction medium are excised from the explant and transferred to the initial development medium for the seedlings containing a cytokinin, for example BAP, and then to the medium of the MB6 type.

According to another embodiment of the invention, explants of plants belonging to the species Cucumis melo are transformed by *Agrobacterium tumefaciens* and the transformed explants thus obtained are then cultivated in the induction medium for shoot buds. The buds are then subjected to the step entailing the development of the transgenic plantlets which, as already explained, takes place in two stages, the second of these stages being performed in the medium of the MB6 type. Finally, the transgenic seedlings thus obtained are cultivated by methods already known from the development of non-transformed plantlets in order to produce transgenic plants.

Figure 1:
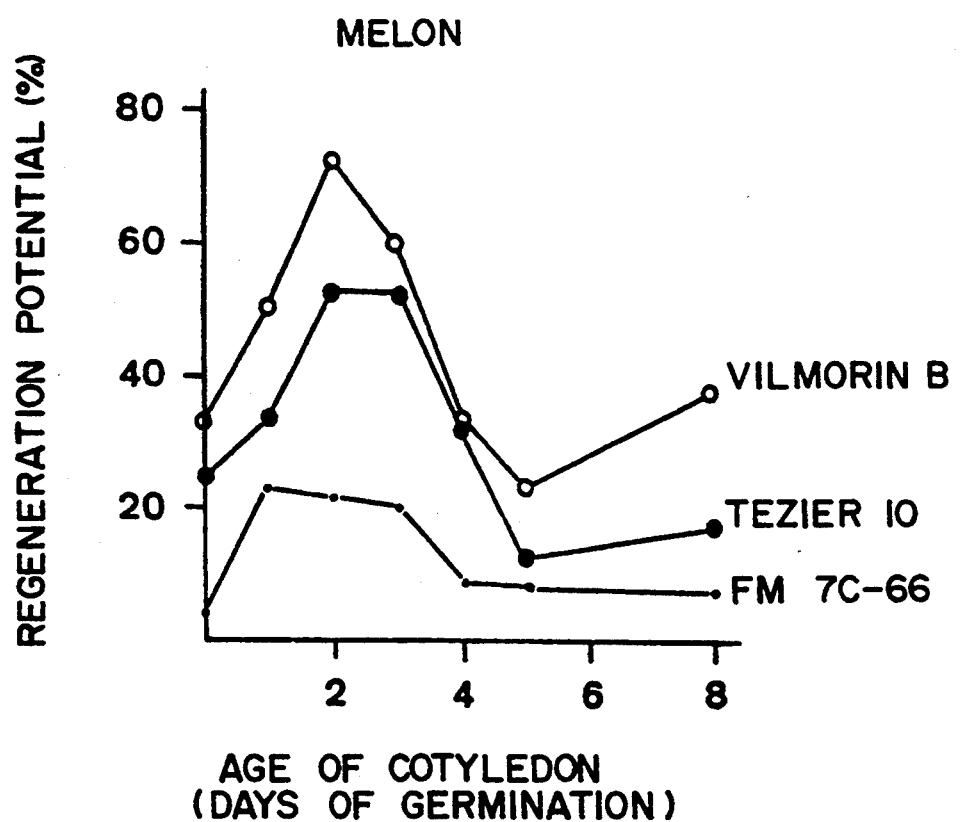
FIG. 1 is a plot of regeneration potential (%) (y-axis) vs. age of cotyledons in days of germination (x-axis) showing the influence of the age of cotyledons on the regeneration percentage of different genotypes.

The explant used as starting material for the transformation and regeneration of transgenic melons may be any explant which can be transformed by *Agrobacterium tumefaciens*, for example: cotyledons, hypocotyls, leaves. The use of cotyledons as explant is particularly advantageous. The inventors have observed that the regeneration potential of buds on cotyledons taken from embryos which have been in culture for up to four days and, in particular, for two days is superior to that shown by younger or older cotyledons (see FIG. 1). This phenomenon has been observed in many different varieties. It is important to specify that the cotyledons are derived from embryos which have germinated for 0 to 4 days, the embryos being isolated from mature melon seeds. Germination from seeds does not lead to the same favourable results. The germination medium is preferably 0.8% (weight/volume) of agar-agar in sterile water, which may be supplemented with 50 μm CoCl$_2$ or NiCl$_2$, which appears to improve the induction of the shoot buds-in the next step. As indicated above, the duration of germination is from 0 to 4 days. A duration of at least three days and in particular of two days is particularly preferred. Germination normally takes place under a light intensity of 60 to 80 μEm$^{-2}$s$^{-1}$, and a photo period of 16/24 hours at about 26° C. during the day and 24° C. at night.

The genetic transformation of the melon explant is performed by the placing in contact of a strain of *A. tumefaciens*, for example in the form of a bacterial suspension, and the explant which has sustained an injury, for example a cut. In the case of cotyledons, the placing in contact with the bacteria is carried out when the cotyledons are 0 to 4 days old, and more particularly 2 days old.

The duration of this contact is not critical; for example, it may last from about 30 minutes to one hour, and is performed for example in suspension in M.S. culture medium.

The explants are then dried on sterile filter paper and transferred to a co-culture medium which may be MS medium solidified with agar-agar. The conditions of light intensity and photo period which are employed during the co-culture are usually the same as those as used during the germination step. This co-culture step usually lasts about 48 hours.

Many nopaline- and octopine-producing strains of *A. tumefaciens* are known and can be used for the genetic transformation of the species Cucumis melo.

The inventors have used the octopine-producing strain LBA4404 containing the Ti plasmid pAL4404 plus the binary vector pGA472 provided by G. Ann, Washington University (Ann et al., 1985) or the nopaline-producing strain C58'3 (Ben Tahar and De Both, 1988). These strains have been cured of their vector and the binary vector pBI121 (provided by R. Jefferson, Plant Breeding Institute) (Jefferson et al., 1987) was introduced into the strain LBA4404 not containing the vector pGA472. This binary vector possesses a gene marker for resistance to kanamycin and a "reporter" gene, the gene for β-glucuronidase coding for an enzymatic activity. This gene for resistance to kanamycin contains the coding region for the gene for neomycin phosphotransferase isolated from the transposon Tn5 flanked at the 5' and 3' by the promoter and terminator of the gene for nopaline synthase. The coding region for the gene for β-glucuronidase is flanked by the promoter for the 35S RNA of the cauliflower mosaic virus and the terminator of the nopaline synthase gene.

The LBA4404 strain containing the vector pBI121 is stored at −20° C. in 15% glycerol. This strain grows on a LB medium containing 50 mg/L kanamycin.

After the co-culture step, the transformed explants are transferred to the shoot bud induction-medium described in the preceding paragraphs. This medium is usually supplemented with agents which allow the selection of transformants, for example kanamycin, and agents which inhibit the growth of A. tumefaciens, for example cefotaxime.

The inventors have observed that the use of "Falcon" ® Petri dishes 9 cm in diameter gives particularly favourable results at the bud induction step. The conditions of light intensity and photo period which are employed during this step are the same as those used during the germination step, a light intensity of 80 $\mu$E.M$^{-2}$s$^{-1}$ being particularly preferred.

Shoot buds develop directly on the explant and when they have attained a size which allows them to be handled physically (about 0.2–1.5 mm, and more particularly 0.5 mm), they are excised from the explant and transferred to a new medium which usually is that which contains the BAP or another cytokinin and which constitutes the 'initial' culture medium for the development of seedlings.

In a variant of the procedure according to the invention, the duration of the induction step, which usually lasts about 21 days, may be shortened to 14 days. In this case, the shoot buds instead of being transferred directly to the initial medium for the development of the plantlets may be transferred to a MS medium without hormones for one week before being subjected to the plantlet development step.

The plantlet development step takes place in two stages as explained above. The shoot buds grow on this medium and when they have attained a height of about 3 mm to 1.0 cm, they are transferred to the MB6 medium, supplemented with agents for selecting the transformants, for example antibiotics and agents which inhibit the growth of A. tumefaciens. Nonetheless, these agents are not essential for regeneration.

After several weeks in this medium, the transgenic plantlets take root. The plants can then be transferred to pots containing compost and coarse sand (2:1 v/v) as soon as the lateral roots have developed.

According to a preferred embodiment of the invention, a gene coding for the capsid protein of the cucumber mosaic virus is introduced into the melon explant through the intermediary of A. tumefaciens. The invention relates to these sequences and the corresponding RNA sequences (see FIGS. 2 and 3), as well as the fragments of these sequences capable of conferring resistance to the CMV.

This virus is composed of 4 RNAs of different sizes; the gene for the capsid protein of the CMV is present at the 3' end of the RNA 3 and on the RNA 4. The translation of the capsid protein only takes place from the RNA 4, the 3'end of the RNA 3 has exactly the same nucleotide sequence. The gene for the capsid protein of two virulent strains derived from different geographical regions has been isolated and sequenced by the inventors.

In regard to this aspect of the invention, a French virulent strain of CMV, called I17F, and a plasmid (pUC18) containing DNA complementary to the RNA 3 of a virulent strain, the FNY, isolated in New York from infected melons, were used. It is obvious that any other gene could be thus introduced into the melon explants, for example genes coding for the capsid protein of other strains of CMV and of other viruses, the procedure of the invention then making possible the regeneration of the transgenic plant containing this gene.

TABLE 1

| MILIEU B6 | |
|---|---|
| KH$_2$PO$_4$ | 85 mg/l |
| MgSO$_4$.7H$_2$O | 185 |
| CaCl$_2$.2H$_2$2O | 1720 |
| KNO$_3$ | 950 |
| NH$_4$NO$_3$ | 165 |
| MnSO$_4$.H$_2$O | 16,9 |
| KI | 0,83 |
| H$_3$BO$_3$ | 6,2 |
| ZnSO$_4$.7H$_2$O | 8,6 |
| CuSO$_4$.5H$_2$O | 0,025 |
| Na2MoO$_4$.2H$_2$O | 0,25 |
| CoCl$_2$.6H$_2$O | 0,025 |
| FeSO$_4$.7H$_2$O | 27,85 |
| Na$_2$EDTA | 37,25 |
| acide nicotinique | 0,50 |
| Thiamine-HCl | 0,10 |
| pyridoxine-HCl | 0,50 |
| Glycine | 2,0 |
| myo-inositol | 100 |
| saccharose | 10 000 |
| gelrite | 4 000 |
| pH | 5,6 |

EXAMPLES

A) Process for the Production of Transgenic Melon Expressing the Gene for Resistance to Kanamycin and the Gene for β-glucuronidase 1. Germination of the Embryos of Cucumis Melo Mature melon seeds (Cucumis melo L) are used to produce mature embryos. The integument of the seed is removed with a scalpel, care being taken not to damage the embryo. The embryos are sterilized by immersion for 5 seconds in neat ethanol then in 200 ml of a saturated solution of calcium hypochlorite and 0.05% of Tween 80 for 20 minutes with constant shaking. The embryos are then rinsed with 200 ml of sterile water for 20 minutes. The embryos are then dried on filter paper and placed in sterile Petri dishes containing 0.8% (weight/volume) of agar-agar in sterile water. The embryos are allowed to germinate for two days in culture rooms under a light intensity of 60 to 80 $\mu$Em$^{-2}$s$^{-1}$ and a photo period of 16/24 hours at 26° C. during the day and 24° C. at night.

2. The Agrobacterium Tumefaciens Strains and the Transformation Vectors

For the transformation experiments the strain LBA4404 containing the vector pBI121 (described in the preceding pages) is placed in culture in 10 ml of the Luria-Bertani medium without antibiotics with continuous shaking (200 rpm) at 28° C. for 12 hours. This bacterial solution will serve as inoculum for a larger volume of LB (Luria-Bertani medium) (50 ml) supplemented with 100 mg L$^{-1}$ of rifampicin and 50 mg L$^{-1}$ of kanamycin. The LB medium is composed of 10 % of bactotryptone, 5 g of yeast extract and 10 g of NaCl per liter at pH 7.5. This bacterial suspension is shaken continuously at 28° C. for 4 to 5 hours until the optical density is 1 at a wavelength of 660 nanometers. The bacterial suspension is then centrifuged at 4000 rpm for 5 minutes and the pellet is taken up in the same initial volume of MS medium. This solution is ready to be placed in contact with the plant tissue.

3. Transformation Procedure

The cotyledons derived from embryos, which have undergone germination for two days in the medium described in paragraph 1, are removed carefully in order to avoid tissues of the apical meristem. Younger or older cotyledons have a reduced potential for generating shoot buds compared with the cotyledons taken from embryos after two days of culture. This result is shown in the figure (1).

The two days old cotyledons are cut into 4 in the bacterial suspension taken up in the MS medium in order to ensure contacts after the injury, with the LBA4404 strain containing the binary vector pBI121. The cotyledon fragments are left for 30 minutes to one hour in the bacterial suspension. Each fragment is dried on sterile filter paper and transferred to Petri dishes containing the MS medium solidified with 0.8% of agar-agar.

The explants are placed in culture in the culture room in vitro for 48 hours under the conditions of light intensity and photo period described in paragraph 1.

4. Induction of Buds

After the two day co-culture described above, the cotyledon fragments are transferred to a new medium containing MS supplemented with 400 mg.L$^{-1}$ cefotaxime (Roussel-Uclaf), 50 mg.L$^{-1}$ kanamycin sulfate, 1.13 mg.L$^{-1}$ BAP and 0.88 mg.L$^{-1}$ AIA. The presence of cefotaxime is required to inhibit the growth of the bacteria. Kanamycin sulfate is used as agent to select the cells thus transformed. The transformed cells are those which possess in their genome the gene for resistance to kanamycin and the gene for β-glucuronidase described in paragraph 2. The plant hormone BAP added to the culture medium is necessary for the induction of buds at the concentrations described above. On the other hand, the presence of AIA is optional.

The cells thus transformed will induce buds which will develop in 50 mg/1 of kanamycin.

The cotyledon fragments are incubated in growth chambers in vitro under the conditions of light intensity and photoperiod described in paragraph 1.

After 3 to 5 weeks shoot buds develop directly from the cotyledon fragments in the presence of 50 mg.L$^{-1}$ of kanamycin. Using this induction medium, no bud can develop in 50 mgL$^{-1}$ kanamycin starting from non-transformed cotyledon fragments. This effect is shown in FIG. 2.

5. Deveopment of Transgenic Plantlets

When the buds induced directly on the cotyledon fragments cultivated in the medium described in paragraph 3 in the presence of 50 mgL$^{-1}$ of kanamycin reach a height of 0.5 mm, they are excised from the cotyledon fragments. These buds are transferred individually to a new culture medium containing MS supplemented with 0.68 mg.L$^{-1}$ BAP, 400 mg.L$^{-1}$ cefotaxime and 50 mg.L$^{-1}$ kanamycin sulfate. These buds grow on this medium and after 2 to 4 weeks, when they have reached a height of 3 mm, they are again transferred individually, this time into 500 ml culture pots containing 100 ml of MB6 medium (see Table 1) containing 50 mg.L$^{-1}$ kanamycin sulfate and 400 mg.L$^{-1}$ cefotaxime.

In this medium described above, the shoot buds grow to a height of 3 mm and after 4 weeks the transgenic plantlets take root. Once the lateral roots have developed in the medium described above, the plants are transferred into pots containing a mixture of compost and coarse sand (2:1) and placed in culture in a greenhouse. During the first seven days, the plants are protected by a plastic cover in order to maintain a humid atmosphere. The plants are watered daily.

One of the plants thus regenerated, (called 884-5) was induced to flower, followed by self-fertilization. The seeds were collected. Four R1 plants germinated and their transgenic character was confirmed by applying the tests described below.

The first test, which detects the activity of the enzyme β-glucuronidase (GUS), is carried out according to the method of Jefferson et al (1987). Another test involves the induction of calli on a leaf or on a petiole explant in a medium containing kanamycin. The formation of a callus indicates that the plant is transgenic. The concentration of kanamycin necessary in a M.S. medium containing BAP and NAA varies as a function of the hormone concentration and the tissue For example in a M.S. medium supplemented with 1 mgL$^{-1}$ of BAP and NAA, (Naphtalene acetic acid), 100 mgL$^{-1}$ of kanamycin are sufficient to inhibit the formation of callion leaves or petioles.

The presence of the foreign genes in the regenerated plants was also tested with the polymer see chain reaction (P.C.R.) (see Lassher et el., 1989; De Both 1990) using 2.5 units of Taq polymersee. The primers used enabled the GUS gene and the NPT gene to be amplified simultaneously. The PCR was carried out only on the R1 generation in order to avoid false positives due to the presence of Agrobacteria in the regenerated tissue.

B) Production of Transgenic Melons Expressing a Gene for Resistance to the Herbicide Phosphinotricine The binary vector pIB16.1 (Hoechst, GbmH, Frankfurt, FRG) carries the neogene and the pat gene (phosphinothricine acetyl transfarase), which confers resistance to phosphinothricine.

The procedure for transformation and regeneration described in example A was used for the production of plants of the Vedrantais genotype, transformed by the vector. The transgenic character of the plants thus obtained confirmed by the test involving callus formation, and hybridization with probes for neo according to the method of Southern.

These plants were self-fertilized and the seeds thus obtained germinated in a greenhouse. The plants thus obtained were subjected to a treatment with the herbicide and some of them proved to be resistant.

C) Production of Transgenic Melons Expressing the Capsid Protein of the Cucumber Mosaic Virus (CMV)

In the examples which follow, a French virulent strain of CMV, called I17F and a plasmid (pUC18) containing the DNA complementary to the RNA3 of a virulent strain, called FNy, isolated in New York from infected melons, have served as the source of the genes of the capsid proteins of CMV.

1. Cloning of the Capsid Protein of the Strain FNY

Starting from the restriction map of the plasmid pUC18 containing the cDNA of the RNA 3 established by P. Palukaitis a 1.6 Kb fragment including at the 3' end the sequence of the capsid protein of 1.6 Kb was subcloned in an expression vector, "Blue scribe". This cDNA was subcloned in the vector Blue Scribe (BS+) (catalogue Stratagene) and each subcloned fragment was .sequenced according to the protocol "sequenase R" (version 2 of USB: United States Biochemicals). The sequenced fragments were analysed on a denaturing 6% acrylamide gel such as that described in Maniatis et al. 1982. This gel is then fixed for 10 minutes in 10% acetic acid, dried in a vacuum for 30 minutes at 80° C. and then autoradiographed (Manjarls et al. 1982). The start of the leader sequence of the capsid protein of the FNY strain has the same length as that of the Japanese Y strain (personal communication from P. Palukaitis). The partial sequence of the RNA 4 of the Y strain has been published (Hidaka et al. 1985). By comparison with this sequence we have been able to position the start of the leader sequence of the FNY strain.

The sequence of the capsid protein including the leader sequence, the coding region and the 3' non-coding region is shown in FIG. 2. Starting from this sequence 2 oligonucleotides of 30 bases complementary to the 3' and 5' ends were synthesized and the sequence of the capsid protein was amplified using the PCR (Polymerase Chain Reaction) technique described by Scharf et al. (1986). The amplification product was analysed on a 1% agarose gel to confirm the size of this 1034bp fragment. The 5' and 3' oligonucleotides possess the BamH1 restriction site at their extremeties. Thus, this amplification product can be cloned into the unique BamH1 site of the vector pBIOS3. The pBIOS3 vector constructed in the laboratory of the inventors possesses a promoter and a plant terminator. The 35S promoter is derived from the 35S RNA of the cauliflower mosaic virus and the NOS terminator is derived from the non-coding 3' region of the nopaline synthase gene.

2) Clong of the Capsid Protein of the Strain I17F

Tomato seedlings at the 2-leaf stage were inoculated with the I17F strain of the CMV. 15 days after infection the virus was purified from the infected leaves according to the technique described in the thesis of Dr. G. Marchoux (1975). The quality of the viral RNA (RNA 1, 2, 3 and 4) is checked on a 1% agarose gel. Once it has been controlled, a DNA complementary to the 4 RNAs is synthesized using the Amersham kit "cDNA Synthesis System plus". The radioactive DNA complementary to the 4 RNAs is loaded onto a 1% agarose gel. After migration of these DNAs, the gel is dried in a vacuum and then is autoradiographed (Maniatis et al. 1982). These complementary DNAs possessing blunt ends are then cloned into the SmaI site of the dephosphorylated pUC18 plasmid (Maniatis et al. 1982). This plasmid carries resistance to ampicillin. E. coli JM101 bacteria, made competent by the calcium chloride method (Maniatis et al. 1982), are transformed by the pUC18 plasmids containing the DNAs complementary to the viral RNAs. Since the pUC18 plasmid carries resistance to ampicillin the transformed bacterial colonies are selected on Luria Broth medium (Manjarls et al. 1982) supplemented with 100 mg/L of ampicillin, on the one hand, and by the blue staining of the colonies (Maniatis et al. 1982), on the other. The recombinant plasmid is isolated from each colony and purified according to the technique of Birnboin and Doly (Maniatis et al., 1982). The recombinant plasmids are digested with the restriction enzymes EcoRI and BamHI; these enzymes, which cut around the SmaI site, enable the plasmid pUC18, on the one hand, and the complementary DNA, on the other, to be separated by electrophoresis. The digestion products are loaded onto a 1% agarose gel and after migration the plasmids containing a complementary DNA of 1 kb (size of the complementary DNA) are selected. A restriction map obtained using the enzymes HindIII, SalI and HindII has made it possible to identify the recombinant plasmids possessing the DNA complementary to the RNA 4 by comparison with the map for the D strain published by Cuozzo et al (1988). The clone possessing the gene coding for the capsid protein was recloned between the EcoRI and BamHI restriction sites of the Bluescribe plasmid (BS+ and BS−) (Stratagene catalogue). Shorter fragments were recloned in the Blue scribe vector and the single-stranded DNA of each of these recombinant plasmids was prepared according to the technique described by Stratagene. The sequence of these different cloned fragments was determined according to the technique described in the protocol "sequenase R" version 2 of USB United States Biochemicals. The sequenced fragments were analysed on a denaturing 6% polyacrylamide gel (Maniatis at el. 1982). The gel is then fixed for 10 minutes in 10% acetic acid, then dried in a vacuum at 80° C. for 30 minutes and autoradiographed (Maniatis et al. 1982). The sequence of the capsid protein of the I17F strain is shown in FIG. 3.

The sequence of the capsid protein is then excised from the recombinant plasmid by digestion with the restriction enzymes EcoRI and BamHI. BamHI linkers are added to the ends of the sequence (Maniatis et al. 1982) which is then cloned into the BamHI sites of the dephosphorylated pBIOS3 plasmid (Maniatis et al. 1982). This sequence, which codes for the capsid protein, is thus placed between the 35S promoter and the NOS terminator.

3. Induction of the Genes Coding for the Capsid Proteins of CMV (Strains I17F and FHY Respectively) in Melon Cotyledones and Regeneration of Transgenic Plants The 2 genes coding for the capsid proteins (I17F and FNY) placed between control sequences are then cloned separately in the binary vector pBI121 (Jefferson et al., 1987) modified by suppression of the EcoRI site at the 3' of the GUS gene, and the creation of a EcoRI site at the HindIII site. These modifications make it possible to insert the cassette promoter—structural gene—terminator derived from pBIOS3.

This latter vector is then introduced into the strain LBA 4404. The Agrobacterium strains containing the binary vector which possesses, on the one hand, the sequence of the capsid protein of the FNY strain (pBIOS132) and, on the other, of the I17F strain (pBIOS135) are used to infect melon cotyledons at the 2-day stage as described in example A. The procedure for the regeneration of the transformed cotyledons is the same as that described in example A. The melon plants, regenerated in a selective medium containing 100 mg/L kanamycin, are analysed. The transgenic character of the regenerated plants was confirmed by the detection of GUS activity and by the technique of callus formation as described in example A.

The expression of the capsid protein of the I17F strain was detected in a plant by a "Western blot" analysis using antibodies against the intact I17F strain. The capsid protein expressed represented about 0.01% of the total soluble protein in the leaves.

The transformed plants are then allowed to go to seed. These transformed plants are demonstrated to be resistant to the cucumber mosaic virus.

FIG. 5 is a "Western blot" showing the immunoreactive bands detected with antibodies against the CMV strain I17F.

BIBLIOGRAPHY

ABAK K, DUMAS DE VAULX R. (1980)—Cucurbit Genetics Cooperative Report 3:27–29

ANN G., WATSON B. D., STACHEL S., GORDON M. P., EW N. (1985)—EMBO J. 4:277–284.

BEN TAHAR S., DE BOTH M. T. J. (1988)—Introduction of foreign genes into melon (Cucumis melo L. ) using *Agrobacterium tumefaciens*. Proc. Cucurbitaceae. France.

BEVAN M. (1984)—Nucleic Acid Research 12: 8711–8718.

BOUABDALLAH L., BRANCHARD M. (1986)—Z. Pflanzenzüchtung 96:82–85.

BRANCHARD M., CHATEAU M. (1988)—C. R. Acad. Sci Paris 307, Série III:777–780.

BROADBENT L. (1976)—Ann. Rev. Phytopathol. 14:75.

CADE R. M., WEHNER T. C., BLAZICH (1988)—Cucurbit Genetics Cooperative Report 11:3–4.

CHEE P. P., TRICOLI D. M. (1988)—Plant Cell Reports 7: 274–277.

CHILTON M. D., TEPPER D. A., PETIT A., DAVID C., CASSE DELBART F., TEMPE J. (1982)—Nature 295: 432–434.

COSTA A. S., MULLER G. W. (1980)—Plant Dis. 64:538.

CUOZZO M., O'CONNEL K. M., KANIEWSKI W., FANG R. X., CHUA N. H. ET TUMER N. E. (1988)—Biotechnology 6:549–557.

DAVID C., CHILTON M. D., TEMPE J. (1984)—Biotechnology 2:73–76.

DEAKIN J. R., BOHN G. W., WHITAKER T. W. (1971)—Economic Botany 25:195–211.

DE BOTH M. T. J., BEN TAHAR S. (1989)—Proc. Inter. Eucarpia Congress on Genetic Manipulation in Plant Breeding New York: Plenum Press (in press).

DE BOTH M. T. J., (1990) Gene Transfer by electroporation to plant protoplasts and tissues. Thesis University of London.

DEGREEF W., DELON R., DEBLOCK M., LEEMANS J., BOTTERMAN J. (1989)—Biotechnology 7:61–64.

DIRKS R., VAN BUGGENUM M. (1989)—Plant Cell Reports 7:626–627.

FERNOW K. H. (1967)—Phytopathology 57:1347.

FRALEY R. T., ROGERS S. G., HORSCH R.B., EICHHOLTZ D. E., FLICK J., FINK C., HOFFMAN N., SANDERS (1985)—Bio Technology 3:629–637.

FRALEY R. T., ROGERS S. G., HORSCH R. B. (1986)—Genetic transformation in higher plants. CRC Critical Rev. Plant Sciences 4:1–46.

HILDER V. A., GATEHOUSE A. M. R., SHEERMAN S. E., BARKER R. F., BOULTER D. (1987)—Nature 300:160–163.

HIDAKA S., TSUNASAWA S., YOON J. O., NARITA K., TAKANAMI Y., KUBO S., MIURA K. I. (1985)—J. Biochem. 97: 161–171.

HOEKEMA A., HUISMAN M. J., MOLENDIJK L., VAN DE ELZEN P. J. M., CORNELISSEN B. J. C. (1989)—Biotechnology 7: 273–278.

HORSCH R. B., FRY J. E., HOFFMAN N. L., WALLROTH M., EICHHOLTZ D. Z., ROGERS S. G. ( 1985 )—Science 227: 1229–1231.

JEFFERSON R. A., KAVANAGH T. A., BEVAN M. W. (1987) EMBO Journal 6:3901–3907.

JELASKA S. (1972)—Planta (Berl.) 103:278–280.

JELASKA S. (1974)—Physiol. Plantarum 31:257–261.

KATHAL R., BHATNAGAR S. P., BHOJWANI S. T. (1986)—J. Plant Physiol. 126:59–62

KATHAL R., BHATNAGAR S. P., BHOJWANI S. T. (1988)—Plant Cell Report 7:449–451.

KEVERS C., COUMANS M., COUMANS-GILLES M. F., GASPAR T. (1984)—Physiol. Plant. 61:69–74

KHO Y. O., DEN NIJS A. P. M., FRANKEN J. (1980) Euphytica 29:661–672.

KIM S. G., CHANG J. R., CHA H. C., LEE K. W. (1988) Plant Cell Tissue Organ Culture 12:67–74.

KLEE H., HORSCH R., ROGERS S., (1987)—Ann. Rev. Plant Physiol 38:467–486.

LASSNER M. W., PETERSON P., YODER, J. I., (1989) Plant. Molec. Rep. 7, 116–128.

LESHEM B., SHALEY D. P., IZHAR S. (1988)—Annals of Botany 61:255–260.

MACKAY W. A., NG T. J., HAMMERSCHLAG F. A. (1988) Cucurbit Genetics Cooperative report 11:33–34.

MALEPSY S., NADOLSKA-ORCZYK N. (1983)—Z. Pfanzenphysiologie 111:273–276.

MANIATIS T., FRITSCH E. F. ET SAMBROOK J. ( 1982 ) Molecular cloning a laboratory manual.

MARCHOUX G.—These de Docteur es Science naturel-les (1975)—"Proprietes biologiques et genetiques des ARN du virus de la mosaique du concombre".

MORENO V., GARCIA-SOGO M., GRANELL I., GARCIA-SOGO B., ROIG L. A. (1985)—Plant Cell Tisue and Organ Culture 5:139–146.

MSIKITA W., SKIRVIN R. M., JUVIK J. A., SPLITTSTOESSER W. E. (1988)—Cucurbit Genetics Cooperative Report 11: 5–7.

MURASHIGE T., SKOOG F. (1962)—Physiologia Plantarum 15:473–497.

NIEDZ R. P., SMITH S. C., DUNBAR K. B., MURAKISHI H. H., STEPHENS C. T. (1989)—Plant Cell Tissue and Organ Culture (in press).

ORIDATE T., OOSAWA K. (1986)—Japan J. Breeding 36: 424–428.

ORTS M. C., GARCIA-SOGO B., ROCHE M. V., ROIG L. A., MORENO V. (1987)—Hort Science 22:666.

POWEL ABEL P., NELSON R. S., DE B., HOFFMANN N., ROGERS S. G., FRALEY R. T., BEACHY R. N. (1986)—Science 232: 738–743.

RAJASEKARAN K., MULLINS M. G., NAIR Y. (1983)—Annals of Botany 52:417–420.

SHARF S. J., HORN G. T., ERLICH H. A. (1986)—Science 233:1076–1078.

SMITH S., DUNBAR K., NIEDZ R., MURAKISHI H. (1988) Abstract Proc. Annual TCA Meeting, Las Vegas, Nev., June 1988.

STABA E. J. (1969)—"Plant tissue culture as a technique for the phytochemist" in "Recent advances in phytochemistry Vol. 2". Ed. :Seikel and Runeckels. Appleton century-crofts, New York.

TUMER N. E., O'CONNEL K. M. NELSON R. S., SANDERS P. R., BEACHY R. N., FRALEY R. T., SHAH D. M. (1987)—Embo J. 6: 1181-1188.

VAECK M., REYNAERTS A., HOFTE H., JANSENS S., DE BEUCKELEER M., DEAN C., ZABEAU M., VAN MONTAGU M., LEEMANS J. (1987)—Nature 328:33–37.

VAN DUN C. M. P., BOL J. F. (1988)—Virology 167: 649–652.

WEHNER T. C., LOCY R. D. (1981)—HortScience 16: 759–760.

VAN RAAMSDONK L. W. D. (1989)—Prophyta 6:231–232.

We claim:

1. Process for the production of transgenic plantlets having diploid phenotype from genetically transformed explants, said plantlets belonging to the species Cucumis melo and containing at least one gene introduced by the intermediary of *Agrobacterium tumefaciens*, comprising the following steps: (a) inducing genetically transformed shoot buds from cotyledons of Cucumis melo in a shoot bud induction medium without forming calli, wherein the cotyledons are obtained from embryos which have germinated from 0 to 4 days before being contacted with *A. tumefaciens*, wherein the induction medium comprises about 440 to about 2,200 mg/L$^{-1}$ of calcium chloride calculated as $CaCl_2.2H_2O$, and about 0.3 to about 1.13 mg/L$^{-1}$ 6-benzyl aminopurine (BAP), and
   (b) forming genetically transformed plantlets from genetically transformed shoot buds, wherein the step of forming comprises:
      (i) culturing the genetically transformed shoot buds in a medium having 6-benzyl aminopurine (BAP) until the shoot buds have reached a height of at least 3 mm; and
      (ii) transferring and incubating the shoot buds in a suitable macro-element plant cell culture medium sufficiently to form the genetically transformed plantlets.

2. Process for production of transgenic plantlets with a diploid phenotype, from genetically transformed explants, said plantlets belonging to the species *Cucumis melo* and containing at least one gene introduced by the intermediary of *A. tumefaciens* comprising the following steps:
   (a) inducing genetically transformed shoot buds from cotyledons of *Cucumis melo* in a shoot bud induction medium without forming calli, wherein the cotyledons are obtained from embryos which have germinated from 0 to 4 days before being contacted with *A. tumefaciens*, and wherein the induction medium comprises about 440 to about 2,200 mg/L$^{-1}$ of calcium chloride calculated as $CaCl_2.2H_2O$, about 0.3 to about 1.13 mg/L$^{-1}$ of 6-benzyl aminopurine (BAP); and about 0 to about 1.3 mg/L$^{-1}$ indole-3-acetic acid (IAA); and
   (b) forming genetically transformed plantlets from the genetically transformed shoot buds, wherein the step of forming comprises:
      (i) culturing the shoot buds in a medium having 6-benzyl aminopurine (BAP) until the shoot buds have reached a height of at least 3 mm; and
      (ii) transferring and incubating the shoot buds in a suitable macro-elements plant cell culture medium comprising:
      $KH_2PO_4$ from about 50 to about 100 mg/L$^{-1}$;
      $MgSO_4$ from about 75 to about 300 mg/L$^{-1}$;
      $CaCl_2.2H_2O$ from about 500 to about 2500 mg/L$^{-1}$;
      $KNO_3$ from about 750 to about 1200 mg/L$^{-1}$; and
      $NH_4NO_3$ from about 150 to about 200 mg/L$^{-1}$ sufficiently to form the genetically transformed plantlets.

3. Process according to claim 2, wherein the shoot bud induction medium comprises the Murashige and Skoog medium supplemented with 0.3 to 1.13 mgL$^{-1}$ of BAP with the proviso that BAP is the only plant hormone present.

4. Process according to claim 2, wherein the shoot bud induction medium further comprises the "Staba" vitamins.

5. Process according to claim 2, wherein the shoot bud induction medium comprises about 1,000 to 2,200 mgl$^{-1}$ $CaCl_2.2H_2O$.

6. Process according to claim 2, wherein the shoot bud induction medium further comprises M.I. medium, having the following composition:

| M. I. Medium | |
|---|---|
| Macro-elements: | |
| $KNO_3$ | 1900 mg/L$^{-1}$ |
| $NH_4NO_3$ | 1650 |
| $CaCl_2 \cdot 2H_2O$ | 2200 |
| $MgSO_4 \cdot 7H_2O$ | 370 |
| $KH_2PO_4$ | 170 |
| $NA_2EDTA$ | as MS |
| Micro-Elements | as MS |
| Vitamins | Staba |
| Myo-inositol | 100 mg/L$^{-1}$ |
| Sucrose | 30 g/L$^{-1}$ |
| Agar-agar | 0.8% |
| BAP | 3.7 µM |
| ABA | 1 µM |

7. Process according to claim 2, where the macro element plant cell culture medium has the following macroelements:

| $KH_2PO_4$ | 85 mg$^{L-1}$ |
|---|---|
| $MgSO_4$ | 185 mg$^{L-1}$ |
| $CaCl_2 \cdot 2H_2O$ | 1720 mg$^{L-1}$ |
| $KNO_3$ | 950 mg$^{L-1}$ |
| $NH_4NO_3$ | 165 mg$^{L-1}$ |

8. Process according to claim 1, wherein the cotyledons are obtained from embryos which have germinated for about 2 days.

9. Process according to claim 8, wherein the genetically transformed shoot buds are formed by the method comprising:
   (a) contacting fragments of cotyledons with a bacterial suspension of *A. tumefaciens*, wherein the *A. tumefaciens* contains a functional gene to be introduced into the plant;
   (b) co-culturing the fragments of cotyledons and the *A. tumefaciens* for about 48 hours.

10. Process according to claim 9, wherein the bacterial suspension is a suspension of bacteria in M.S. medium and the co-culture medium is M.S. medium solidified with agar-agar.

11. Process for the production of transgenic plants belonging to the species *Cucumis melo*, having a diploid phenotype, comprising culturing a transgenic plantlet prepared by the method of claim 1 in a culture medium to form transgenic plants wherein the culture medium provides for the development of non-genetically transformed plants from plantlets.

* * * * *